United States Patent [19]

Lynn

[11] Patent Number: 5,514,117
[45] Date of Patent: *****May 7, 1996

[54] CONNECTOR HAVING A MEDICAL CANNULA

[76] Inventor: Lawrence A. Lynn, 1275 Olentangy River Rd., Suite 223, Columbus, Ohio 43212

[ * ] Notice: The term of this patent shall not extend beyond the expiration date of Pat. No. 5,137,524.

[21] Appl. No.: 361,694

[22] Filed: Dec. 22, 1994

Related U.S. Application Data

[63] Continuation of Ser. No. 982,644, Dec. 1, 1992, abandoned, which is a continuation of Ser. No. 515,466, Apr. 27, 1990, Pat. No. 5,167,643, which is a continuation of Ser. No. 509,638, Apr. 17, 1990, Pat. No. 5,137,524, which is a continuation of Ser. No. 509,639, Apr. 17, 1990, abandoned, which is a continuation-in-part of Ser. No. 264,533, Oct. 31, 1988, abandoned, which is a continuation-in-part of Ser. No. 240,539, Sep. 6, 1988, Pat. No. 4,946,445.

[51] Int. Cl.⁶ ............................................. A61M 25/00
[52] U.S. Cl. ............................................. 604/283
[58] Field of Search ............................. 604/200, 285, 604/86, 905, 411–414, 198, 29, 87, 88, 244, 283

[56] References Cited

U.S. PATENT DOCUMENTS

| | | |
|---|---|---|
| 2,400,722 | 5/1946 | Swan . |
| 3,021,942 | 2/1962 | Hamilton . |
| 3,893,608 | 7/1975 | Koenig . |
| 3,976,073 | 8/1976 | Quick . |
| 4,248,223 | 2/1981 | Turner . |
| 4,248,246 | 2/1981 | Ikeda . |
| 4,366,816 | 1/1983 | Bayard . |
| 4,398,757 | 8/1983 | Floyd . |
| 4,405,163 | 9/1983 | Voges et al. ............... 604/283 |
| 4,432,759 | 2/1984 | Gross . |
| 4,470,575 | 9/1984 | Stoll . |
| 4,474,734 | 10/1984 | Cooper . |
| 4,559,042 | 12/1985 | Votel . |
| 4,573,713 | 3/1986 | Kipp . |
| 4,588,402 | 5/1986 | Igari . |
| 4,636,204 | 1/1987 | Christopherson . |
| 4,654,034 | 3/1987 | Masters . |
| 4,675,020 | 6/1987 | McPhee ............... 604/411 |
| 4,735,617 | 4/1988 | Nelson . |
| 4,740,204 | 4/1988 | Masters . |
| 4,752,292 | 6/1988 | Lopez . |
| 4,759,756 | 7/1988 | Forman et al. ............... 604/88 X |
| 4,768,568 | 9/1988 | Fournier et al. ............... 604/905 X |
| 4,820,288 | 4/1989 | Isono ............... 604/283 |
| 4,834,716 | 5/1989 | Ogle, II . |
| 4,840,618 | 6/1989 | Marvel . |
| 4,852,844 | 8/1989 | Villaveces . |
| 4,895,570 | 1/1990 | Larkin ............... 604/411 |
| 4,919,656 | 4/1990 | Bracker . |
| 4,921,489 | 5/1990 | Frizzell . |

(List continued on next page.)

OTHER PUBLICATIONS

The Deseret Company, Sandy, Utah 84070, Product Profile, Printed in the U.S.A. form D–6395B (Apr. 1979), The Deseret Family of Intermittent Infusion Devices.

*Primary Examiner*—Gene Mancene
*Assistant Examiner*—Jeffrey A. Smith
*Attorney, Agent, or Firm*—Cushman Darby & Cushman

[57] ABSTRACT

A medical connector for manually connecting a fluid conveying conduit that is in fluid communications with a patient's vasculature and having a junction terminal at an end thereof to a fluid conduit for administration of fluid to the patient. The connector is formed of two components. The first component includes a cannula hub to which a cannula is mounted, a base extending from the hub and fingers extending from the base. The second component is a collar including a support and bars extending therefrom. The collar is manually slidable along the first component in the direction the cannula extends between a retracted position and a locking position. The bars engage the fingers to flex into engagement with the junction terminal. The bars are elastically deformable to provide a spring force for locking the fingers on the junction terminal.

15 Claims, 11 Drawing Sheets

U.S. PATENT DOCUMENTS 4,932,944 6/1990 Jagger et al. .
4,946,445 8/1990 Lynn .
4,950,242 8/1990 Alvarez .
4,963,133 10/1990 Whipple ................................ 604/283
5,137,524 8/1992 Lynn et al. ............................. 604/283
5,167,643 12/1992 Lynn .

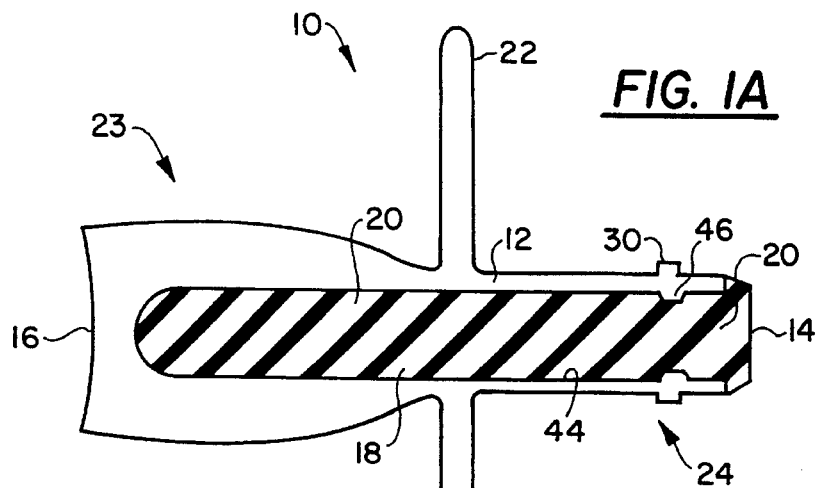
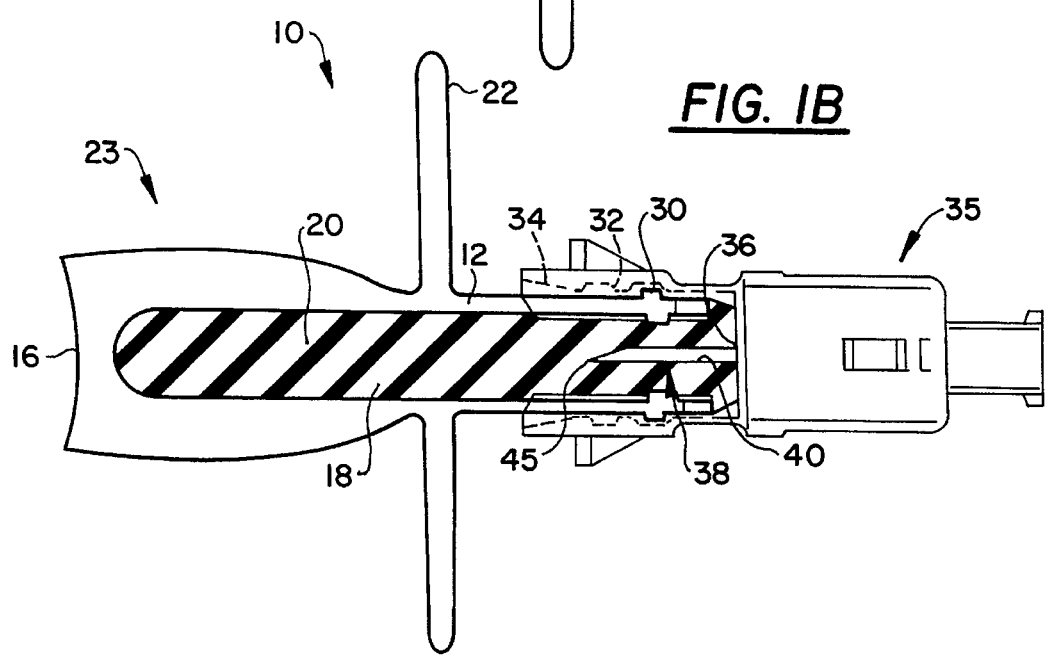
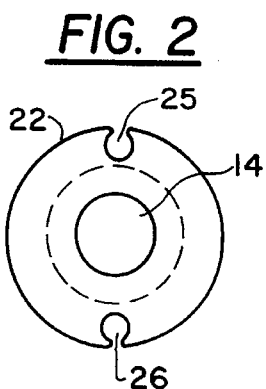
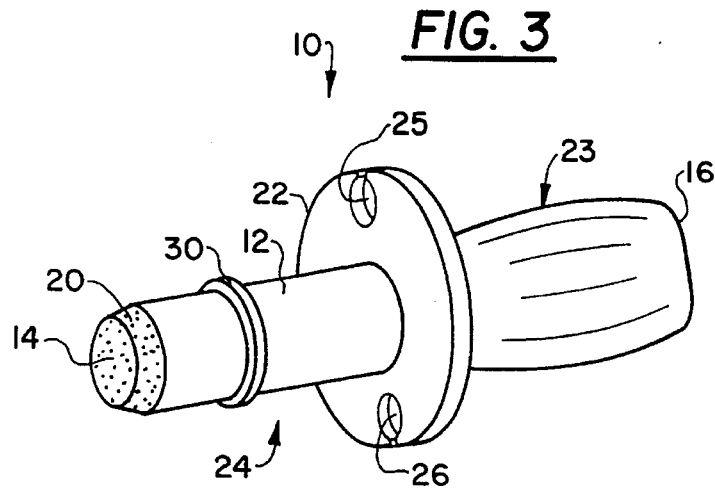

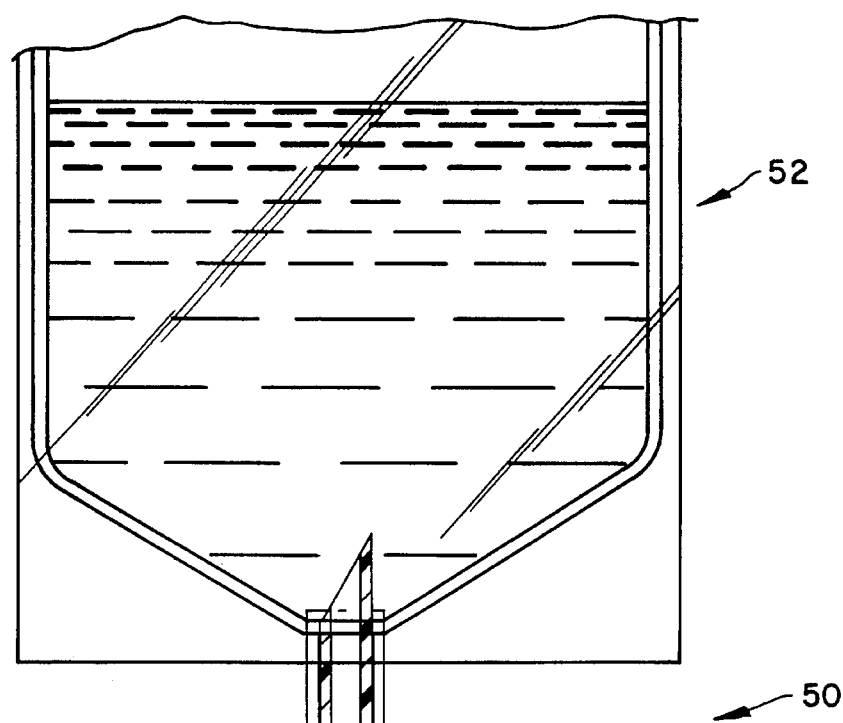
FIG. 4
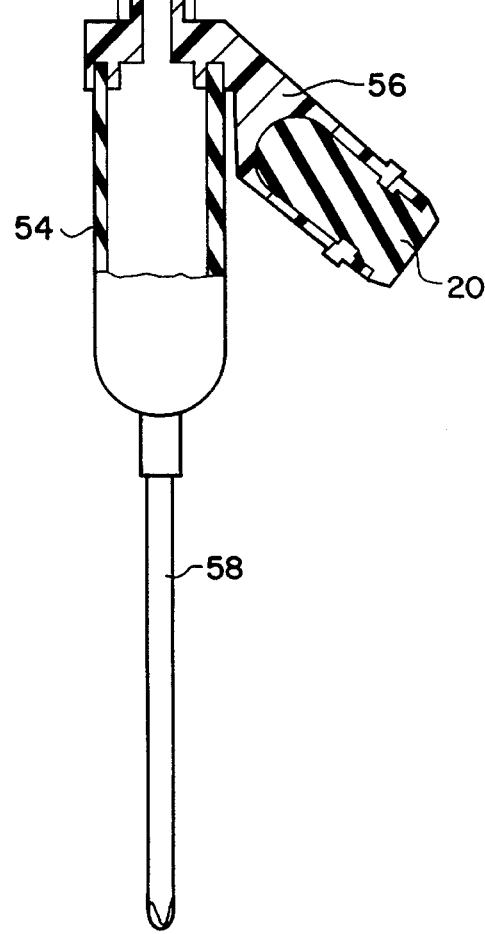

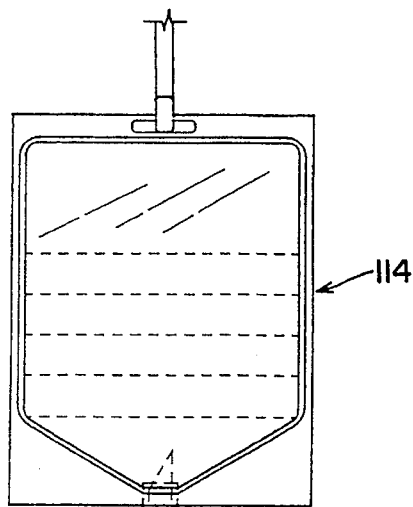
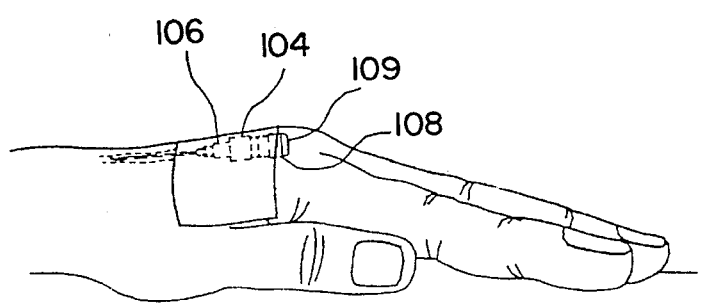
*FIG.8A*
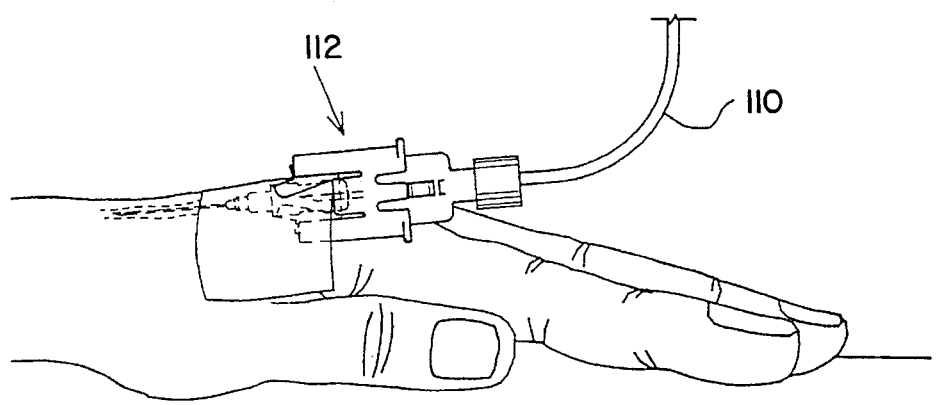
*FIG.8B*

CONNECTOR HAVING A MEDICAL CANNULA

This is a continuation of application Ser. No. 07/982,644, filed on Dec. 1, 1992, which was abandoned upon the filing hereof which was a Cont. of application Ser. No. 07/515,466 filed Apr. 27, 1990, now U.S. Pat. No. 5,167,643, which was a continuation-in-part of application Ser. No. 07/509,638 filed Apr. 17, 1990, now U.S. Pat. No. 5,137,524 which was a Cont. of application Ser. No. 07/509,639 filed Apr. 17, 1990, now abandoned, which was a CIP of application Ser. No. 07/264,533 filed Oct. 31, 1988, now abandoned, which was a CIP of application Ser. No. 07/240,539 filed Sep. 06, 1988 now U.S. Pat. No. 4,946,445.

BACKGROUND AND FIELD OF INVENTION

This invention relates to a novel, reusable medical needle protection station.

The risk of needlestick transmitted infection to hospital personnel is well known. Conventional needles are now universally provided by their manufacturers with a snap on or threaded on hollow cap which is removed just prior to use. A common area wherein needlestick injuries occur is in handling needles after they are temporarily or permanently withdrawn from fluid connection with a patient. In particular, the recapping of needles poses a high risk of needlestick and is now considered a violation of universal precautions and is prohibited by OSHA in the hospital environment.

Unfortunately, it is very difficult for the nurse to deal with the exposed needle after use if the nurse can not cap it. Ideally, the nurse would immediately drop this exposed and contaminated needle into a waste receptacle for disposal. However, such receptacles are not always in close proximity to the nurse at the time of the needle withdrawal and therefore the nurse often has to lay the needle on a table or hold the needle in one hand while she finishes the task at hand. During this time, the nurse is potentially exposed to needlestick risk, as are any other hospital personnel who may come into contact with the needle if it is displaced from the table and becomes lost in a bedsheet or is otherwise contacted. Despite the fact that recapping is forbidden it is in fact a common procedure for the simple reason that no practical alternative is available.

In addition to the needlestick risk to hospital personnel of recapping, the needle itself may become contaminated with microorganisms during .recapping. As the nurse begins to recap the needle, the tip of the needle can easily contact the side of the cap potentially resulting in contamination. In addition, unless the nurse uses a new cap from a sterile package each time the needle is recapped, the original cap is potentially contaminated if the hollow interior of the cap has been exposed to the ambient nonsterile environment for any significant length of time.

Thus, in the administration of piggyback medications, if the nurse chooses to recap, the nurse should use a new cap, each from their own separate sterile package. Indeed, due to the risk of injury of hospital personnel all authorities presently recommend that an entire new needle and cap be utilized each time a piggyback medication is given to a patient despite the additional expense and time required. For economic and practical reasons that procedure often is not followed.

The universal coupler of my U.S. Pat. No. 5,137,524, and which is disclosed hereinbelow, makes recapping without risk of infection to hospital personnel possible because the invention is configured so as to inhibit the digit of the human hand from entering the space which contains the needle. However, even with use of this coupler the other aforementioned problems relative to capping would still exist. In particular, there remains the problem of the interior of caps becoming contaminated after they have been removed from the needle. Therefore, the nurse, to be completely safe, must obtain a new cap each time she recaps my universal connector if the interior of the previous cap has been exposed to the ambient environment for a substantial period of time.

Blunt needles and cannula are now being used in place of the conventional sharp needle because the risk of such a blunt tip piercing the skin is remote. However, the contamination problem with microorganisms during recapping discussed above is still present with these devices.

The invention also relates to a universal medical connector for coupling intravenous conduits.

The attachment of intravenous tubing to intravascular catheters for the administration of fluids and medication to patients has been widely utilized for decades. Generally, an intravenous tubing system comprises a segment of tubing which is distally attached to an intravascular catheter inserted into a patient's blood vessel. Such primary conduits usually have junction terminals at an end which are occluded by a penetrable septum. Such a system acts as a primary conduit system. A secondary conduit may be connected to the primary conduit system for the administration of fluids into he patient. The secondary conduit generally has a fluid source at its proximal end and has an open distal end for attachment to the primary conduit system.

FIG. 8a illustrates a conventional primary conduit with its distal end occluded by a septum. In conventional connection, a needle attached to the open end of a secondary conduit is inserted through the septum of the primary conduit to create fluid connection between the fluid source and the catheter.

Junction terminals and septae come in a wide variety of shapes and sizes. FIGS. 7(a)–(f) illustrate the profile of a number of such conventional junction terminals. Commonly, such junction terminals have a head portion which includes a septum which occludes the distal end of the junction terminal. Such junction terminals generally further comprise a rigid tube which extends to the head bearing the septum. The head diameters vary considerably from as little as a 0.301 inches to as much as 0.389 inches, and may be comprised of stretched latex or rigid plastic. Similarly the tube diameters vary from 0.224 inches to 0.330 inches. The head diameter may be virtually the same as the tube diameter or may be substantially greater than the tube diameter. This great variation makes very difficult a universal connector which can reliably and effectively connect and tightly hold or lock onto almost everything that is available in the hospital or medical environment.

The Ogle U.S. Pat. No. 4,834,716 demonstrates a shielded needle for insertion into a Y shaped junction terminal. However, the Ogle device provides only a shield and does not provide a secure attachment. Lopez et al., U.S. Pat. No. 4,752,292 shows a variety of specifically interfacing devices which include shielded needles intended to provide attachments between primary and secondary tubing systems. However, the disclosed devices have components which must attach to other specific interacting components of a compatible primary system. These devices are not, therefore, compatible with conventional primary systems. Indeed, such devices will not securely attach to the wide range of conventional junction terminals in present use, but rather require the nurse to use a specifically compatible interfacing primary system which may not be readily available. Therefore, none of these devices provides a universal device which can securely lock to the broad range of conventional junction terminals presently in use in medical practice.

SUMMARY OF INVENTION

The present invention comprises a novel, reusable, sterile, sealed needle or cannula protection station. This device provides a reusable means for the maintenance of needle sterility on an intermittent basis and obviates the need for conventional caps. The needle can be "docked" or "minded" at the station during times it is not in use and this reuse and redocking of the needle can potentially continue for as long as 72 hours.

The sterility protection station comprises, in general, a housing having a sterile internal bore, a proximal end, and a distal end. The housing is preferably comprised of relatively hard plastic and is impenetrable even by a sharp steel needle. The distal end is sealed by a sterile elastomeric member which can be pierced by a needle or cannula. The elastomeric member further reseals after removal of a needle or cannula to maintain the sterility of the bore and is preferably formed as a core extending along the length of the bore. The proximal end of the housing is occluded such that the housing forms a fully enclosed tube with the internal bore being proximally dead ended. The proximal dead end is preferably comprised of substantially impenetrable, hard plastic integral with the housing.

A finger shield is preferably provided which is located intermediate the distal and proximal ends of the tube. The transverse width of the housing proximal to the shield is preferably of a diameter which allows the housing to be comfortably held by the thumb and index finger. The portion of the housing proximal to the shield therefore provides a handle for holding the protection station. The shield preferably is comprised of a substantially planner member of hard plastic and protects the fingers holding the handle should the needle slip during insertion into the elastomeric sealing member. The transverse width of the shield is preferably at least two times the diameter of the housing. The shield may be substantially a flat disc extending circumferentially around the housing. Alternatively, the shield may extend in a distal or proximal direction about the housing.

The portion of the housing distal to the shield preferably is formed as a cylindrical tube. The distal end of the tube is occluded by the aforesaid sealing member. A annular detent on the exterior of the tube is preferably provided intermediate the shield and the distal end of the tube for engaging a similar detent when the station is used with my universal connector or with other shrouded devices having detents. The diameter of the tube, the length of the tube distal to the shield, and the distance of the annular detent from the distal end of the tube are preferably matched to allow an optimal interface with the universal connector of my above mentioned patent application as will be described.

The protection station may be free standing and enclosed in a sealed, sterile envelope and individually packaged. Alternatively, the protector may be attached to and comprise an integral part of a secondary intravenous tubing system. For example the station could be formed as part of another molded component such as a flow drip chamber on a secondary intravenous tubing set so that it is always immediately available to the nurse using the set.

In operation, the nurse removes the station from its sterile package by grasping the handle with the thumb and index finger proximal to the shield while holding a needle such as the type enclosed within the connector of my previous application or any other needle or cannula in the other hand. The needle is then inserted into the sterile elastomeric member so that both the needle tip and needle shaft are enclosed within the sterile, dead ended bore. This protects and shields the needle tip and shaft within the sterile and sealed bore of the station. The needle can then be retained within the station until it is again ready for use. When the nurse wishes to reuse the needle the nurse withdraws it from the protection station. Upon withdrawal of the needle, the elastomeric member reseals the original perforation which was caused by the indwelling needle so that the interior of the bore remains sterile for reuse.

During use or when awaiting use, free standing stations may be hung from IV tubing by inserting the IV tubing into notches provided on the shield. Alternatively, the nurse may simply leave the station on a nearby table. When the nurse has finished using the needle and wishes to store the needle in a sterile environment for reuse later, the nurse again grabs the handle of the station with her thumb and index finger and prepares the exposed end of the elastomeric member with alcohol or other suitable antiseptic to cleanse its surface. The nurse then reinserts the needle into the elastomeric member so that the tip and at least a substantial portion shaft of the needle are again enclosed and protected within the sterile bore of the station.

Preferably the entire formerly exposed shaft of the needle is received and protected by the elastomeric member. The elastomeric member preferably extends along the length of the bore so that the needle tip remains within the elastomeric member when the needle is fully advanced. This assures that the needle is occluded at its tip so that substantial fluid from the needle cannot flow from the needle tip into the bore of the station. The station is preferably sized such that the length of the bore which receives the needle is matched with the length of needles intended for use with the station. The stations may be colored or otherwise coded to indicate the longest needle they can fully accommodate. Therefore, the nurse can advance the needle along the entire length of the needle shaft until the distal end of the needle hub abuts the exposed end of the elastomeric member. In this way, the entire length of the needle is protected in a sterile environment and the needle is "minded" for future use. It is intended that a sterile needle may be repetitively reused and stored in this way for up to 72 hours before it is discarded.

The device, therefore, provides a self-sealing, sterile, fully enclosed, needle protection station which can be prepared with antiseptic each time before use. The preferred embodiment both seals the needle at its tip and maintains sterility of the entire length of the needle shaft distal to the hub when the needle is not in use.

The present invention further relates to improvement in a universal medical connector for coupling intravenous conduits.

The universal connector disclosed and claimed in this application is formed of two elements. The first element defines a needle hub adapted to be connected to an open end of a fluid conveying conduit, a needle mounted to the hub, and a base extending from the hub with fingers extending therefrom to define a space through which the needle extends toward an open end, the space being bounded by the fingers.

A second locking element is formed as a collar manually slidable from a retracted position in which a septum can be inserted into the space and penetrated by the needle to locking position flexing the fingers to trap and lock onto the septum. The collar has separated bars which extend along the fingers from a support to flex the fingers as the locking element is slid toward the locking position. In the illustrated embodiment the needle cannot easily or normally be contacted by the digits of a person using the connector.

According to a first aspect of the present invention, the collar is provided with a detent on a detent carrier which engages a corresponding detent and stop on the outer surface of the base. The carrier is preferably formed by slots extending inwardly from the end of the collar. The detent carrier acts like a spring, flexing as it is pushed past the corresponding detent. Thus, the collar can be pushed back and forth innumerable times between retracted and locking positions without wearing out the detent or stops.

According to a second aspect of the present invention, each finger is provided with separated catches on its interior surface for engaging the junction terminal and septum. The inner catch primarily engages larger junction terminals and the outer catch engages the conduit for both larger and smaller junction terminals. The catches are configured so that inadvertent disengaging force to separate the two elements is less dependent on junction terminal diameter. The head of the junction terminal therefore releases at a given range of pull forces upon the coupler which is largely independent of junction terminal diameter. This release mechanism prevents an inadvertent forceful pull on the secondary intravenous tube connected to the coupler (such as might occur when the secondary intravenous tube becomes wrapped around a bed rail) from damaging the junction terminal.

The release mechanism is provided by the relationship between the pair of catches provided along the interior surface of the distal end of the fingers, and the cam interaction with the bars. More particularly, the inner catch, which engages large junction terminal, gradually slopes in the directions of the open end. Since a junction terminal of larger head diameter will be held by a stronger spring force of the bars, the catch angle is less acute to reduce the holding force against inadvertent displacement. Smaller head diameters result in less spring force and, therefore, a sharper angle is provided with the outer catch to increase the holding force against such displacement.

The sharper angle of the outer catch does not substantially hold the larger diameter terminal because this catch is held away from the head by the more proximal inner catch which abuts the side of the head during displacement. Thus, the connector releases at roughly the same applied force which is less dependent of junction terminal diameter.

BRIEF DESCRIPTION OF THE DRAWINGS

FIG. 1a shows a longitudinal sectional view of one embodiment.

FIG. 1b shows the section view of FIG. 1a with the needle universal connector of my co-pending patent application Ser. No. 07/509,638 (now U.S. Pat. No. 5,137,524) received into the station.

FIG. 2 shows a top plan view of the embodiment of FIG. 1a.

FIG. 3 shows a perspective view of the embodiment of FIGS. 1a and 2.

FIG. 4 shows a portion of a secondary intravenous tubing system having an integral station and drip chamber.

FIG. 8(a) shows a conventional primary conduit, in this case a short heparin well, connected to a catheter within a patient's vein. The primary conduit is shown covered by tape except for the tip bearing the septum.

FIG. 8(b) shows the primary conduit of FIG. 8(a) connected to a secondary conduit by the connector of the present invention.

DESCRIPTION OF THE PREFERRED EMBODIMENT

Figure 5:
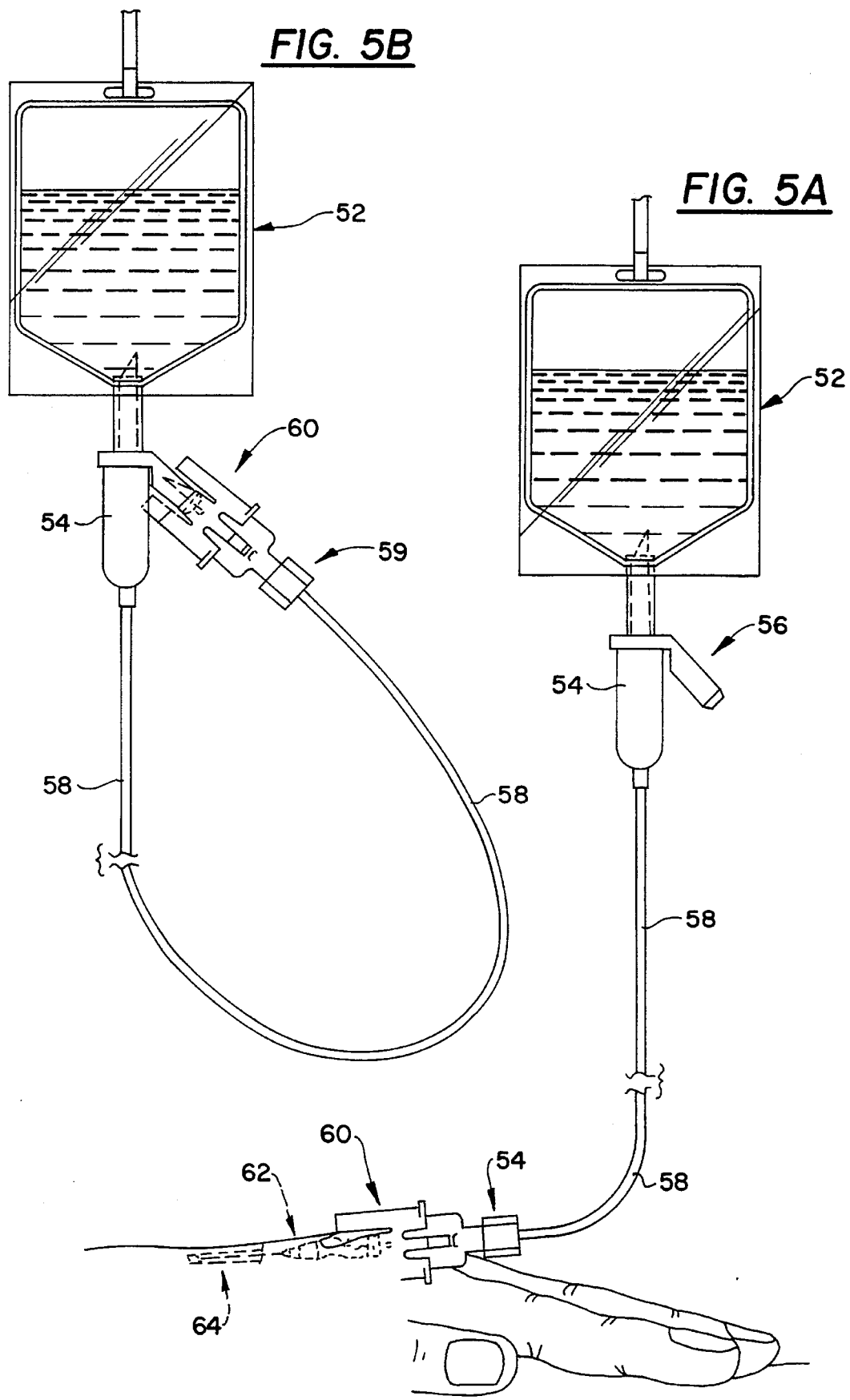
FIG. 5a shows the secondary intravenous tubing set of FIG. 4 connected to a primary intravenous system within the vein of a patient by the connector of my previous invention.
FIG. 5b shows the connector of FIG. 5b docked at the protection station and awaiting reuse.

Reference is now made to a first embodiment of the protection station 10 shown in FIGS. 1 through 3. Housing 12 is provided with a distal end 14 and a dead-ended proximal end 16 and an internal bore 18 extending from the distal end toward the proximal end. An elastomeric sealing member 20 is provided at the distal end 14 of the bore 18 and extends into bore 18 in the direction of the proximal end 16 of the housing 12. Preferably elastomeric member 20 extends to a position adjacent the closed proximal end 16 of housing 12. An integral finger shield 22 is provided intermediate the proximal and distal ends 14 and 16 of the housing 12 effectively dividing the housing into a handle portion 23 and distal tube 24. The handle portion 23 is preferably at least 1.5 cm and the distal tube at least 1 cm in length.

As can best be seen in FIG. 2, Shield 22 has a pair of notches 25 and 26 each having a pincer-like configuration. Any suitable number of notches can be provided. These notches are sized so that a conventional intravenous tube can be squeezed past the pincers into the notch and tightly held by the notch so that the station can be, in effect, detachably hung to conventional intravenous tubing at any point along its length.

The shield 22 diameter is preferably at least two times greater than the maximum width of the handle 23 so that adequate finger protection is provided during operation. An annular detent 30 is provided on housing 12 intermediate shield 22 and the distal end 14. As shown in FIG. 1b, detent 30 is positioned so that a finger detent 32 on the interior wall of fingers 34 on the a connector 35, is positioned on the proximal side of the housing detent 30 and abutting the housing detent 30. The detent 30 is spaced from the distal end 14 of housing 12 at a distance which is slightly less than the distance from the detent 32 on the interior wall of the fingers 34 to the septum stop 36. Therefore, when the needle 38 is completely advanced so that the previously exposed shaft 40 of the needle 38 is completely within elastomeric member 20, the detent 32 of the internal wall of the fingers 34 is slightly distal to housing detent 30. This allows the station 10 to be securely held by the detents 30 and 32 in a position wherein the formerly exposed needle shaft 40 and tip 45 are completely covered by the elastomeric member 20 and the tip 45 is occluded by member 20.

Preferably the elastomeric member 20 and housing 12 are insert molded together. The interior surface 44 of housing 12 is provided with an inwardly protruding extension 46 for fixing the elastomeric member 20 in place within the bore 18. Elastomeric member 20 further extends beyond the distal end 14 of housing 12 to aid in optimal preparation with antiseptic.

Figure 6:
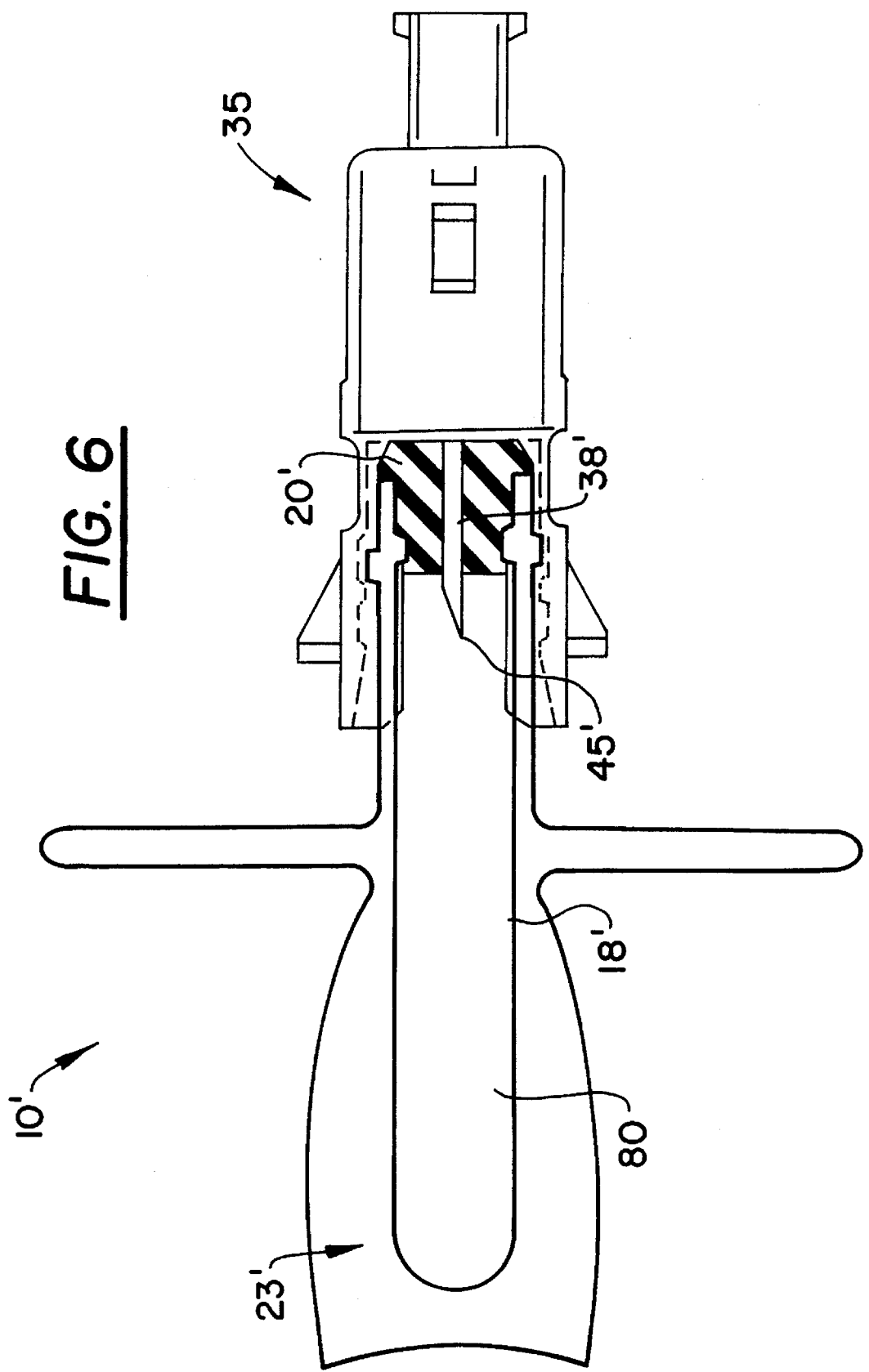
FIG. 6 shows an embodiment wherein the bore is partially hollow.
Figure 7A:
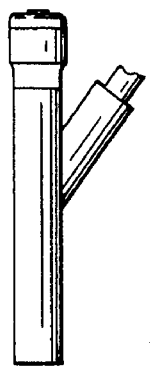
FIGS. 7(a)–7(f) show the profile for a number of typical septae and terminals illustrating the variable configurations.
Figure 7B:
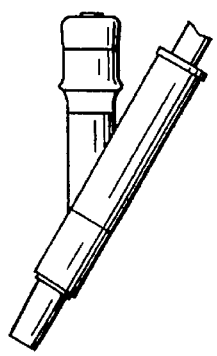
Figure 7C:
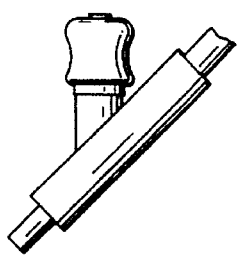
Figure 7D:
Figure 7E:
Figure 7F:
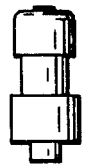

In a modification, as shown in FIGS. 4 and 5, the station can be molded as an integral portion of a secondary intravenous tubing system 50. FIG. 4 shows a fluid source such as a bag of intravenous fluid 52 connected to a drip chamber 54 having an integral station 56 extending downward away from drip chamber 54. FIG. 5a shows the intravenous tube or conduit segment 58 of system 50 attached at its open distal end 59 to connector 60 which is in turn connected to a primary intravenous system 62 and catheter 64 with the vein of a patient. In this embodiment, station 56 is fixed in a position along the proximal one half of the length of a secondary intravenous set so that the intravenous tubing can be easily folded back upon itself and distally connected to the station for storage as in FIG. 5b. In another modification as shown in FIG. 6 a free standing station 10' is shown having shortened elastomeric member 20' within bore 18'. Bore 18' extends proximal to elastomeric member 20' producing a dead ended chamber 80 within a hollow handle 23'. Needle tip 45' of needle 38' is shown within chamber 80. The remainder of the structure is similar to the structure of FIGS. 1–3.

One of the primary advantages of the present invention is that it is reusable without losing sterility. However, if a user wants to discard after a single use, the simplicity and low cost of this invention make that practical. It is of course possible that, for certain patients, single use may be desirable.

FIG. 8(b) shows a view of the unique connector of the present invention forming part of a system for supplying intravenous fluid to a patient. Primary conduit 104 is shown attached to catheter 106 (shown with its tip in the vein of the dorsun of a patient's hand). Primary conduit 104 has a conventional junction terminal 108 having a septum 109 (the junction terminal 108 is shown partially covered by tape as in typical operation.) Secondary conduit 110 is coupled to primary conduit 104 by the universal connector 112 of the present invention, thereby placing bag 114 in fluid communication with the patient's vein.

Reference is now made to FIGS. 9 through 15 which illustrate a preferred embodiment of the connector of the present invention. Connector 112 is formed of two distinct elements.

Figure 15:
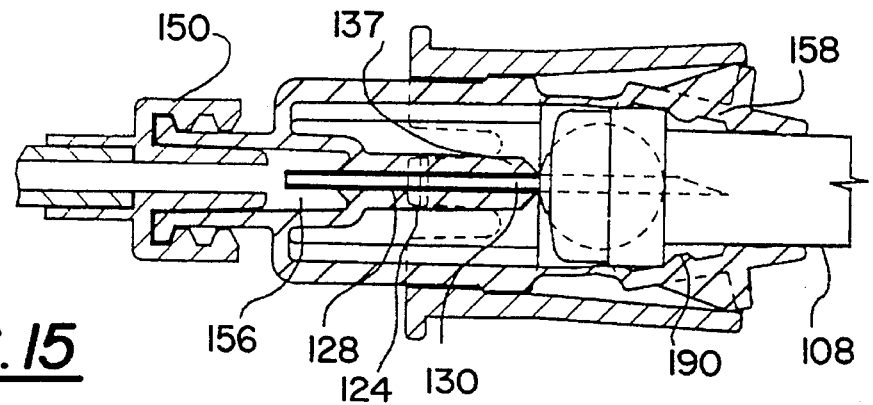
FIG. 15 shows a sectional view of the assembled connector coupling an open ended conduit to a junction terminal and septum having a large head and a large tube.

Element 122 integrally forms a needle hub 124, a base 126 having an inner passage 128 as shown in FIG. 15 through which a cannula, e.g., a needle 130 extends from the proximal hub 124 and a pair of fingers 132 and 134 extending from the base 126 in the direction that the needle 130 extends and bounding an inner space or cavity 136 through which the needle 130 extends. Preferably the base 126 and 124 are integral, but may be formed separately and attached by adhesive or otherwise. The space or cavity 136 is preferably cylindrical having a length of 0.661 inches and a diameter of 0.436 inches. The pro- mal end of space 136 is defined by base 126 comprising septum stop 137 as shown in FIG. 15. The length of needle 130 proximal to septum stop 137 is preferably about 0.627 inches. The length of needle 130 from the septum stop to the needle point is about 0.466 inches.

The locking element is integrally formed as a collar 138 having a support portion 140 and further having a pair of arcuate bars 142 and 144 extending therefrom and a pair of shields 146 extending between the bars 142 and 144 from the support portion and separating bars 142 and 144.

Both elements 122 and 128 are formed of a suitable plastic material such as PCTG which is a polyester, a polycarbonate and PCTG blend sold under the trademark EKTR, or an acrylic mutipolymer sold under the trademark CYRO LITE. All these materials are reactively rigid and suitable for use in a medical environment and can be sterilized in accordance with conventional techniques.

Needle hub 124 provides a flange 148 at the proximal end thereof which is readily and conventionally attachable to open ended conduits 150 (FIGS. 15 and 16) of the type now used in hospitals and elsewhere for connection to bottles and bags of fluid and to pumps providing fluid to be administered into a patient's vein. The distal end 152 of the needle hub 124 remote from the flange 148 is integrally connected to base 126. Base 126 has detent 154 on the exterior surface hereof as can be best seen in FIG. 10. Thus, the lumen through element 122 includes the hub 124 and the cannula, e.g., the needle 130.

Figure 16:
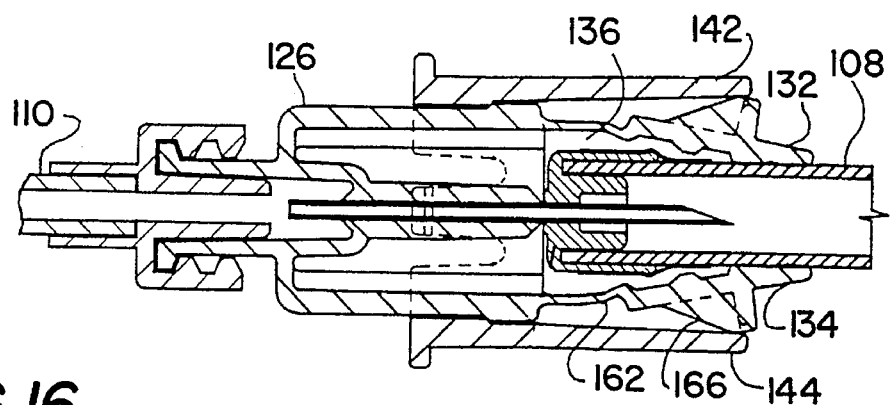
FIG. 16 shows a sectional view on the assembled combination coupled to a junction terminal having a smaller head and tube, and wherein the head diameter is minimally greater than that of the tube.

Needle 130 is conventionally coupled to needle hub 125 and extends through a passage 156 in the needle hub 124 as best seen in FIGS. 15 and 16. A pair of arcuate fingers 132 and 134 integrally extend from the distal end 157 of base 126 (remote from its joinder to needle hub 124) to respective fingertips. Fingers 132 and 134 are formed with distal segments 158 and 160 respectively joined to base 126 by connecting segments defining connecting weakened segments 162 and 164. The connecting segment 162 is preferably between 1 mm and 10 mm in length, preferably less than 5 mm, and preferably greater than 3 mm.

In this embodiment two fingers are provided, but more can be used if desirable or necessary. Preferably the fingers are identical. In operation the fingers flex inwardly with considerably less force than required to make them flex outwardly. Equally important, the fingers spring back to substantially their initial position when the inward force is removed.

Figure 9:
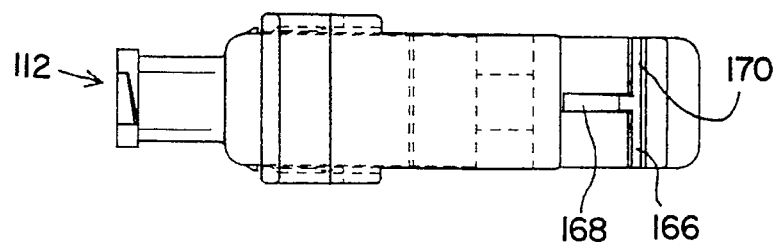
FIG. 9 shows a side view of the assembled combination.
Figure 10:
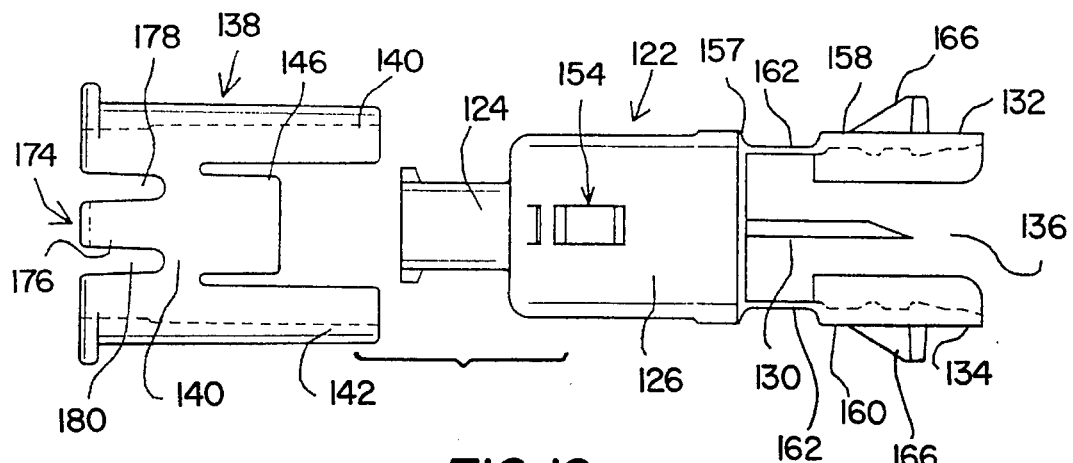
FIG. 10 shows a top view with the locking element separated from the element defining the needle hub, base, and fingers.

Fingers 132 and 134 bound the inner space 136 through which the needle 130 extends and in the illustrated embodiment serve to protect users of connector 112 from inadvertent needle stick. On the exterior surface of each of the fingers 132 and 134 is provided a cam portion 166 which is formed as a narrow ramp 168 terminating in a transverse ridge 170 forming with ramp 168 a T-shaped cam portion 166 as can be seen in FIGS. 9 and 10. Ramp 168 is spaced back from the fingertips of fingers 132 and 134 by a distance which is preferably at least 1 mm and nor more than 10 mm. The width of the ramp is preferably about 0.5 mm, but can be 0.4 mm or less or, 0.6 mm or even greater.

A narrow ramp is advantageous in limiting the force which must be applied to overcome friction when the locking element 138 is manually shifted form the retracted to the locking positions as will be described hereafter. The ramp height is preferably approximately 3 mm, but may range from 0.5–5 mm or greater depending on the distance the cam is set back from the tips of the fingers. The angle of the ramp is preferably about 30 degrees.

When the collar 138 is assembled with element 122 as illustrated in FIGS. 11–15, detent 154 engages a corresponding hook-like detent 174 on the interior surface of a detent carrier 176, the carrier 176 is formed by slots 178 and 180 extending into support 140. In operation, detent carrier 176 can flex as collar 138 is slid along base 126.

The arcuate bars 142 and 144 each preferably extend no more than 90° about the periphery of the support and base. Alternatively, the bars may be straight posts. The preferable maximum outward flexing of the bars induced by the wedging force of cam 166 is about 0.0885 inches in this embodiment.

In order to lock the connector of the present invention on to a junction terminal 108 having septum 109, the junction terminal 108 is inserted into the space 136 bounded by fingers 132 and 134 so that the needle 130 penetrates septum 109 of terminal 108 and effects fluid communication between the open end 150 of conduit 110 coupled to needle hub 124 and the catheter 106 coupled to the junction terminal 108 of the primary intravenous conduit 104 as shown in FIG. 8(b). When junction terminal 108 is maximally advanced septum 109 will about septum stop 137 as shown in FIGS. 15–17.

FIGS. 15–19 show the connector of the present invention locked onto various kinds of typical junction terminals. For example as shown, when the collar 138 is manually pushed in the direction of the open end of the space 136 through which needle 130 extends, bars 142 and 144 slide along the fingers 132 and 134 and engage cam portion 166 causing fingers 132 and 134 to flex inwardly. A flexure therefore is defined along the connecting weakened segments 162 and 164 intermediate the base 126 and distal segments 158 and 160. For a large junction terminal 108, such as shown in FIG. 15, the bars 142 and 144 may, in fact, flex slightly outward as the fingers 132 and 134 flex inward. For a smaller junction terminal like that shown in FIG. 16, of course, the flexing of the fingers 132 and 134 will be greater inwardly and the flexing of the bars 142 and 144 outwardly less or non-existent. It is the combination of potential outward flexion of the bars and inward flexion of the fingers which allows the connector to lock onto a wider range of junction tube diameters.

Figure 11:
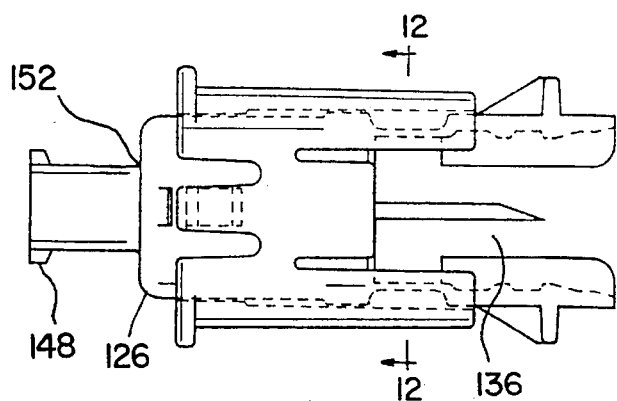
FIG. 11 shows a top view of the assembled combination with the locking collar in the retracted position.
Figure 12:
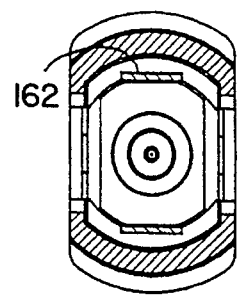
FIG. 12 shows a sectional view of FIG. 11 along the lines 12—12.
Figure 13:
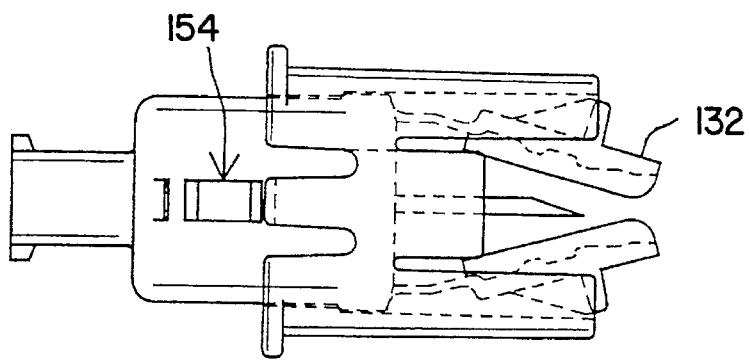
FIG. 13 shows a top view of the assembled connector in the locking position.
Figure 14:
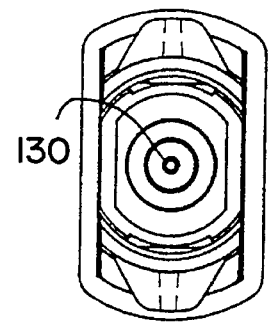
FIG. 14 shows an end view of FIG. 11.

Thus, bars 142 and 144 cooperate with fingers 132 and 134 to define an elastically deformable spring when the collar is moved into the locking position. The spring is deformable, from an original undeformed shape in its retracted position, illustrated, for example, in FIG. 11, by forcible interaction between the junction terminal, the fingers 132 and 134 and the bars 142 and 144 when the junction terminal has been received into the cavity, the collar is moved into its locking position and the fingers are inhibited from flexing inwardly by contacting the junction terminal, as illustrated in FIG. 15. The bars, of course, rebound to their original undeformed shape, as illustrated in FIG. 11, when the collar is returned to its retracted position.

Figure 17:
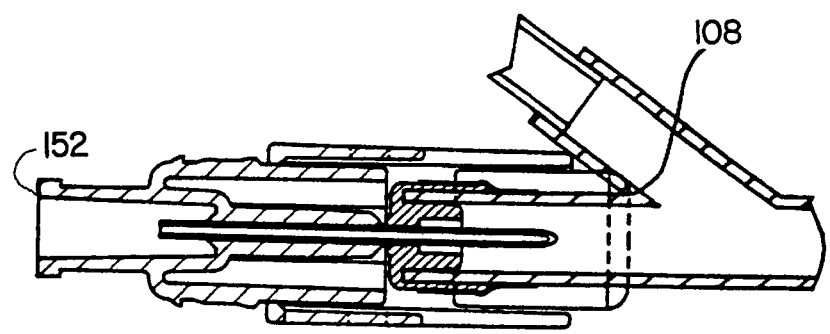
FIG. 17 shows a sectional view of the assembled combination with the locking element in the locking position upon a Y-shaped junction terminal.
Figure 18:
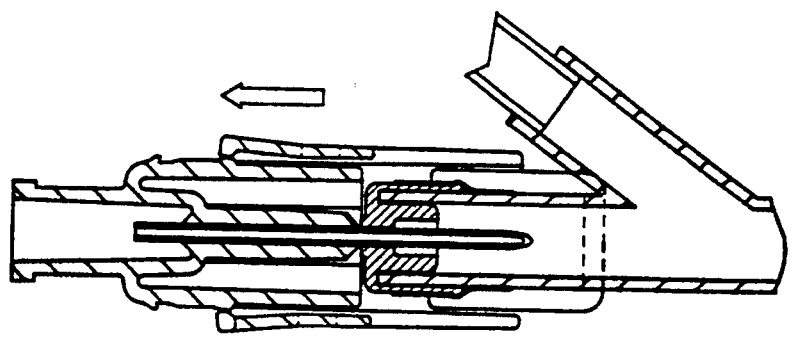
FIG. 18 shows a sectional view of the assembled combination and Y shaped junction terminal of FIG. 17 with the locking element being retracted.
Figure 19:
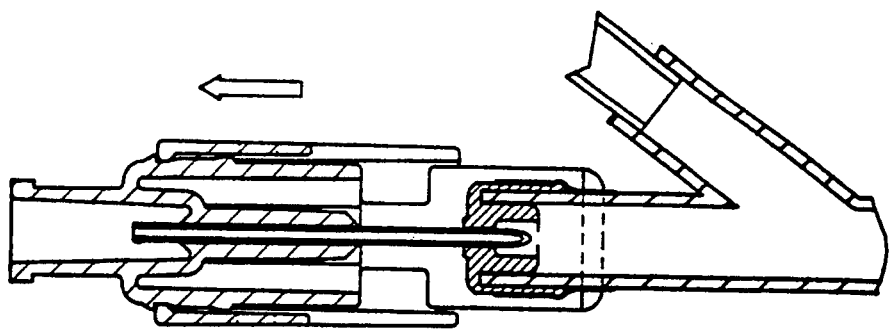
FIG. 19 shows the assembled combination and Y-shaped junction terminal of FIGS. 17 and 18 with the locking element fully retracted against the proximal stop.

FIGS. 17 through 19 illustrate how the connector 112 is released as the collar 138 is manually moved between the locking position illustrated in FIG. 17 and the retracted position illustrated in FIG. 19. The junction terminal 108 in this instance is a convention Y-junction.

Figure 20:
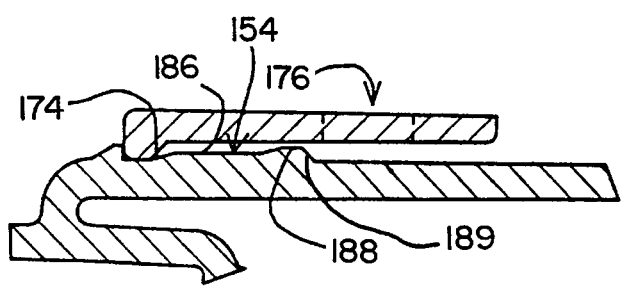
FIG. 20 shows a detailed sectional view illustrating the proximal stop and the detents.

FIG. 20 shows in detail the detent 154 on the base 126 and the corresponding detent 174 on detent carrier 176. The detent 174 on the detent carrier 176 comprises a hook-shaped portion extending downwardly as shown from the end of the detent carrier 176. The detent on the base 126 is formed as a proximal portion 186 with a rising slope which gradually rises to a maximal height at a summit 188 and then abruptly declines in a distal portion 189 back to the original elevation. Making the gradual scope in the direction of movement toward the locking position and the abrupt slope in the opposite direction ensures that minimal force only need be applied to slide collar 138 distally thereby reducing the risk of damage to the vein by pushing too hard on the catheter, while at the same time ensuring that much grater force is required to manually slide the collar 138 in the opposite direction to the retracted position so that inadvertent disconnection is avoided.

Figure 21:
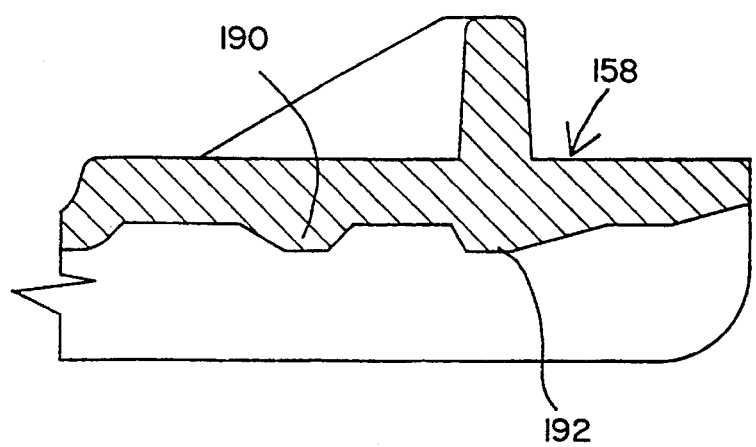
FIG. 21 illustrates a detailed view of the inner and outer catches on each finger.

Reference is now made to FIG. 21 which illustrates distal segment 158 of one of the fingers 132 and 134 with inner and outer catches 190 and 192. Inner catch 190 is formed with a gradual slope 191 in the direction of the distal end. As shown, for example, in FIG. 15, inner of inner catch 190 compensates so that an inadvertent and extremely forceful pull (such as might occur if the secondary tubing inadvertently became wrapped around a bed rail) will allow the connector 112 to disengage from the junction terminal without destroying the junction terminal. Conversely for a small junction terminal, the spring force is less, but the abrupt slope of catch 192 holds the small junction terminal better. The larger junction terminal 108 is not held by the outer catch 192 during a forceful inadvertent pull because inner catch 190 rides over junction terminal 108 swinging outer catch 192 outwardly. Thus, the force necessary to inadvertently disengage without retracting collar 138 is less dependent of junction terminal diameter because the outer catch 192 has a sharper angle than said inner catch 190.

Figure 22:
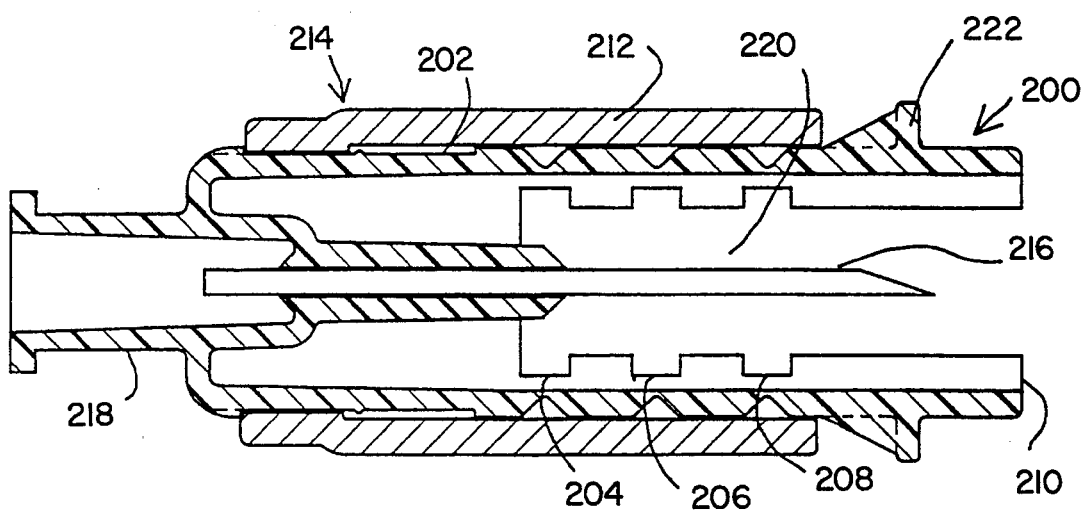
FIG. 22 shows a further embodiment in which a plurality of flexing regions are provided along the length of each finger.

FIG. 22 illustrates an embodiment in which a plurality of weakened regions are provided for gripping a junction terminal by flexing inwardly at different points to provide even greater universality. Each finger 200 extending from base 202 has three weakened regions 204, 206 and 208 between its point of connection to base 202 and its tip 210. As in the other embodiments, regions 204, 206 and 208 are preferably covered by bars 212 extending from collar 214 in the retracted position. Needle 216 extends from hub 218 into space 220 as in the other embodiments. Bars 212 engage cam 222 as described above.

Figure 23A:
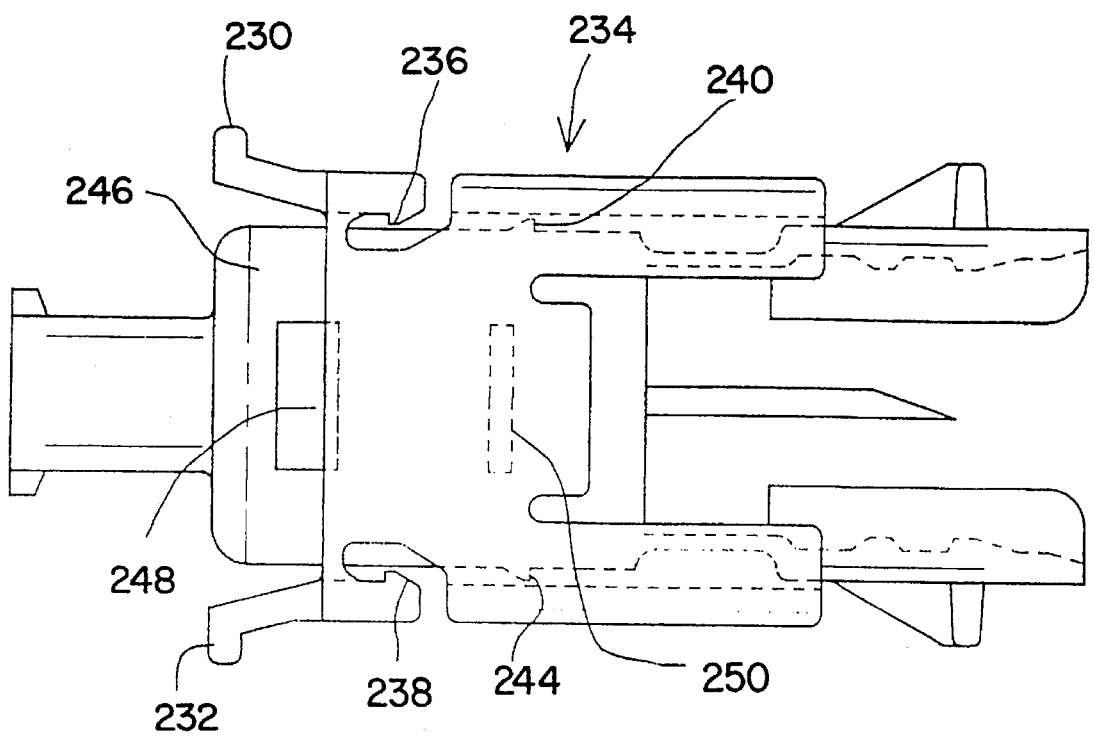
FIGS. 23(a) and (b) show a further embodiment in which the detent carrier flexes outwardly when squeezed.
Figure 23B:
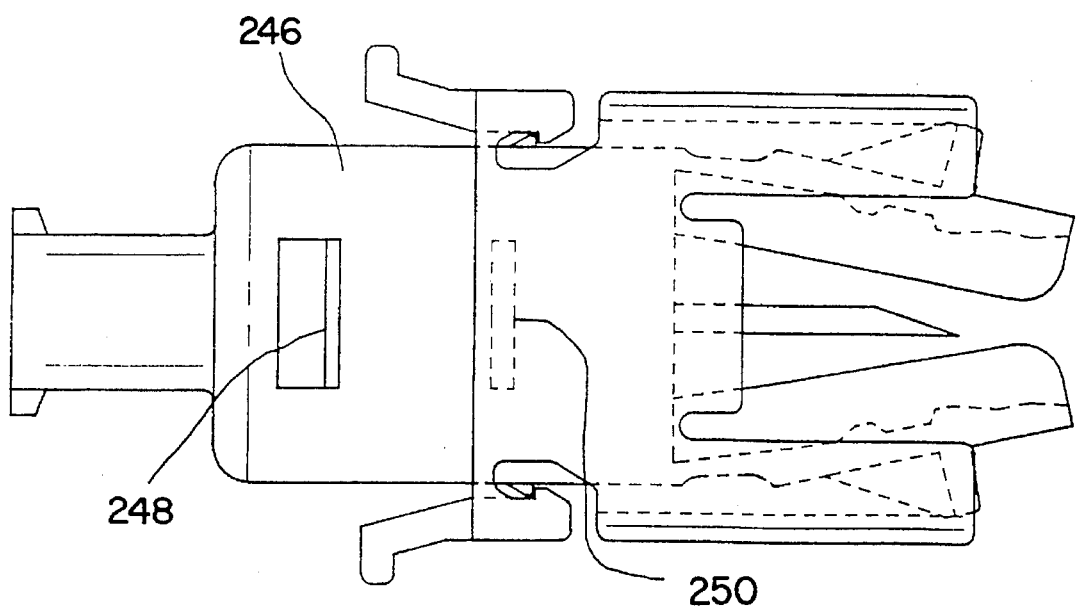

FIGS. 23(a) and 23(b) illustrate a further embodiment in which the force required to slide the collar to the locking position is further minimized. This is achieved by a pair of attached lever arms 230 and 232 which extend outward from collar 234. Arms 230 and 232 respectively have catches 236 and 238 which are pivoted beyond detent 240 and 244 when arms 230 and 232 are manually squeezed. Alternatively, the collar 234 can be slid with catches 236 and 238 riding over the respective detents without squeezing lever arms 230 and 232. However, collar 234 cannot readily be retracted without squeezing so some further security against inadvertent disconnection is provided. In this extended position, collar 234 can be slid without resistance to the locking position shown in FIG. 23(b) engaging detents 242 and 244 of base 246. Stops 248 and 250 are provided on base 246 and function as described above. The other elements and details are as described above.

Many changes and modifications can of course be carried out without departing from the spirit of the invention. The chamber 80 could be filled with a sterilizing solution such as alcohol. Further, if desired, for use with blunt cannulas, the elastomeric member may have a centrally positioned perforation extending along its longitudinal axis for receiving a blunt cannula or needle. In respect to the inventive connector, furthermore, the connector could be permanently affixed to an open ended conduit. Also, the connector can be used with junction terminals which have a pre-perforated septum such as a slit for receiving a bunt cannula. Alternatively, the needle may be a blunt cannula which penetrates such pre-perforated septum or slit. Accordingly, the claims which follow are intended to define the invention.

I claim:

1. A medical connector for connecting a secondary intravenous tubing system having an open end to a primary intravenous tubing system having a junction terminal, the junction terminal including a tube defining an axis having an outer axial surface and a bore extending to a junction end, the junction end being occluded by an elastic sealing member, the connector comprising:

a. a base having a first open end and a lumen extending through said base, said base having means for connecting to said open end of said secondary tubing, b. a cannula extending axially from said base, said lumen extending through said cannula from said base, c. at least two cantilevered fingers extending axially from said base and about said cannula, at least the distal portions of said fingers being moveable from (1) a first, resting position wherein said junction end can be received between said fingers and said cannula can penetrate said sealing member so that said lumen of said cannula is in fluid communication with said bore, to (2) a second, flexed position wherein said junction terminal is received by said fingers so that displacement of said junction terminal from between said fingers when inadvertent retraction force is applied to one said primary system and said secondary system is substantially prevented, d. a collar slidable along said connector from, (1) a retracted position allowing said fingers to rest in said first position to, (2) an advanced position, said collar engaging said fingers to flex said fingers from said first position to said second position when said collar is moved from said retracted position to said advanced position, e. each said finger having a cam defined thereon, said collar engaging said cam upon displacement of said collar toward said advanced position, engagement by said collar deflecting at least the distal portion of the respective finger toward said flexed position.

2. The connector of claim 1 wherein only two fingers are provided, said fingers being oppositely opposed to flex directly toward each other when said collar is moved to said advanced position.

3. The connector of claim 1 wherein said sealing member includes a portion covering said outer surface adjacent said end and wherein said fingers have a proximal portion and a distal portion and wherein said proximal portion is narrow and further wherein said distal portion is wide, said narrow portion defining a flexion region and said wide portion defining a gripping region, said wide portion gripping adjacent said covered portion of said junction terminal when said junction terminal is inserted between said fingers and said collar is moved to said advanced position.

4. The connector of claim 1 wherein said base includes upper and lower walls separating said fingers and wherein said upper and lower walls are flat so that said connector has a low profile.

5. The connector of claim 1 wherein said junction terminal sealing member includes a portion covering said outer surface adjacent said end and has an end face adjacent said junction end and wherein said connector includes a stop connected to and about said cannula, said stop preventing further advancement of said terminal when said face engages said stop, said cannula including a portion projecting from adjacent said stop, said fingers projecting axially beyond said stop for a greater distance than the length of said covering portion of said elastic member so that said fingers project beyond said covering portion when said junction terminal is maximally advanced between said fingers.

6. The connector of claim 1 wherein said sealing member includes a portion covering said outer surface adjacent said end and has a distal end adjacent said end of said junction terminal, and wherein said covering portion of said sealing member has a proximal annular end, said proximal end defining an elevated annular lip adjacent said longitudinal wall of said tube, said fingers engaging said lip when one said primary system and said secondary system is inadvertently pulled away from the other.

7. A connector as in claim 1, further comprising an assembly which prevents said collar from being advanced beyond said advanced position.

8. A connector as in claim 1, wherein at least a portion of said collar is elastically distortable to define a spring force resiliently urging said fingers against said junction terminal, whereby when any of a variety of transverse sizes, shapes, external configurations, and rigidities of junction terminals are received between said fingers, said collar can be moved to said advanced position and said junction terminal will be held tightly by said fingers.

9. A medical connector for connecting a secondary intravenous tubing system having an open end to a primary intravenous tubing system having a junction terminal, the junction terminal including a tube defining an axis having an outer axial surface and a bore extending to a junction end, the junction end being occluded by an elastic sealing member, the connector comprising:

a. a base having a first open end and a lumen extending through said base, said base having means for connecting to said open end of secondary tubing.

b. a cannula extending axially from said base, said lumen extending through said cannula from said base, c. at least two cantilevered fingers extending axially from said base add about said cannula, said fingers being moveable from (1) a first, resting position wherein said junction end can be received between said fingers and said cannula can penetrate said sealing member so that said lumen of said cannula is in fluid communication with said bore, to (2) a second, flexed position wherein said junction terminal is held tightly by said fingers, said fingers gripping said junction terminal to prevent displacement of said junction terminal from between said fingers when inadvertent retraction force is applied to one said primary system and said secondary system, d. a collar slidable along said connector from (1) a retracted position allowing said fingers to rest in said first position, to (2) an advanced position, said collar engaging said fingers to flex said fingers from said first position to said second position when said collar is moved from said retracted position to said advanced position, at least a portion of said collar being elastically distortable to define a spring force resiliently urging said fingers against said junction terminal, whereby when any of a variety of transverse sizes, shapes, external configurations, and rigidities of junction terminals are received between said fingers, said collar can be moved to said advanced position and said junction terminal will be held tightly by said fingers, and wherein said open end of said base includes a female luer connector sized to receive an open male connector defined at said open end of said secondary intravenous tubing system, the female connector having a flange defined on an outer portion thereof for threading attachment to a female end defined about said male connector of said secondary tubing.

10. The connector of claim 9 wherein said collar includes a support and first and second opposed cantilevered bars projecting axially from said support and overlying said fingers when the collar is in said advanced position, said bars deflecting said fingers from said first position to said second position when said collar is moved from said retracted position to said advanced position, each said bar being elastically displaceable outwardly relative to said support to define said spring force when said collar is moved to said advanced position.

11. A medical connector for connecting a secondary intravenous tubing system having and open end to a primary intravenous tubing system having a bore, said primary system further including a junction terminal, said terminal comprising a tube having an end and defining a longitudinal axis, said tube having rigid side walls, said terminal end being occluded by an elastic sealing member, the connector comprising:

a. a base having a first open end and a lumen extending through said base, said base having means for connecting to said secondary tubing adjacent said first open end, said base further having first and second generally flat side walls, b. a cannula extending axially from said base, said lumen extending through said cannula from said base, c. two directly oppositely disposed cantilevered fingers extending axially from said base and about said cannula, said fingers having arcuate distal ends, said fingers being moveable from, (1) a first position wherein said covered portion of said junction terminal can be received between said fingers and said cannula can penetrate said sealing member so that said lumen of said cannula is in fluid communication with said bore of said primary intravenous tubing system and, (2) a second position wherein said junction terminal is held tightly by said fingers, said fingers gripping tightly against said rigid side walls to prevent displacement of said junction terminal from between said fingers when one said primary system and said secondary system is accidentally pulled away from the other, d. a collar slidable along said connector from (a) a retracted position allowing said fingers to rest in said first position to (b) an advanced position, said collar engaging said fingers to flex said fingers from said first position to said second position when said collar is moved from said retracted position to said advanced position, said collar having arcuate portions for selectively overlaying said arcuate distal ends of said fingers and flat portions for selectively overlaying said flat side walls of said base, whereby the connector can lie flat against a flat surface.

12. A medical connector for connecting a secondary intravenous tubing having an open end to a primary intravenous system having a bore, said primary system further having a junction terminal, the junction terminal having a rigid outer wall defining a longitudinal axis, the junction terminal further having an open end, the junction end being occluded by an elastic sealing member, the connector comprising:

a. a base having a first open end and a lumen extending through said base, said base having means for connecting said secondary tubing adjacent said secondary tubing end, b. a cannula extending axially from said base, said lumen extending through said cannula from said base, c. said connector including at least two cantilevered fingers extending axially from said base and about said cannula, at least the distal portions of said fingers being moveable from (1) a first position wherein said junction terminal can be received between said fingers and said cannula can penetrate said sealing member so that said lumen of said cannula is in fluid communication with said bore of said primary intravenous tubing system and (2) a second position wherein said junction terminal is received by said fingers so that displacement of said junction terminal from between said fingers is substantially prevented, d. a collar slidable along said connector from (a) a retracted position allowing said fingers to rest in said first position to (b) an advanced position, said collar engaging said fingers to flex said fingers from said first position to said second position when said collar is moved from said retracted position to said advanced position, said collar having an elastically deformable distal end, said collar and said fingers interacting to define a spring force, said spring force being directed transversely to said wall axis and inwardly against said rigid outer junction terminal wall to cause said fingers to squeeze against said longitudinal outer surface of said junction terminal to prevent displacement of said junction terminal from between said fingers, said spring force being induced by interaction between said collar and said fingers when said collar is moved to said advanced position and when said fingers are inhibited from flexing inwardly by said wall, said distal end of said collar being elastically deformed outwardly by said interaction with said fingers, said collar elastically resisting said deformation to define said spring force directed against said fingers to cause said fingers to grip against said longitudinal outer surface of said junction terminal, said spring force causing tight gripping frictional engaging force between said fingers and said junction terminal, said frictional force preventing inadvertent longitudinal disengagement of said connector and said junction terminal, e. each said finger having a cam defined thereon, said collar engaging said cam upon displacement of said collar toward said advanced position, engagement by said collar deflecting at least the distal portion of the respective finger toward said flexed position.

13. The connector of claim 12 wherein said junction terminal further includes a covered portion defining an elevated lip adjacent said longitudinal sidewalls, said fingers engaging said lip when said junction terminal has been received between said fingers and when said collar is moved to said advanced position and when at least one said primary and said secondary system is inadvertently pulled away from the other, both said gripping spring force and said engagement with said lip comprising combined forces, said forces inhibiting displacement of said junction terminal from between said fingers.

14. A medical connector for connecting a secondary intravenous tubing having an open end to a primary intravenous system having a bore, said primary system further having a junction terminal, the junction terminal having an outer wall defining a longitudinal axis, the junction terminal further having an open end, the junction end being occluded by an elastic sealing member, the connector comprising:

a. a base having a first open end and a lumen extending through said base, said base having means for connecting said secondary tubing adjacent said secondary tubing end, b. a cannula extending axially from said base, said lumen extending through said cannula from said base, c. said connector including at least two cantilevered fingers extending axially from said base and about said cannula, at least the distal portions of said fingers being moveable from, (1) a first resting position wherein said junction terminal can be received between said fingers and said cannula can penetrate said sealing member so that said lumen of said cannula is in fluid communication with said bore of said primary intravenous tubing system and, (2) a second position wherein said junction terminal is received by said fingers so that displacement of said junction terminal from between said fingers is substantially prevented, d. a collar slidable along said connector from, (a) a retracted position allowing said fingers to rest in said first position to, (b) an advanced position, said collar engaging said fingers to flex said fingers from said first position to said second position when said collar is moved from said retracted position to said advanced position, said collar and said fingers interacting to define a spring force, said spring force being directed inwardly against said junction terminal wall to cause said fingers to squeeze against said longitudinal outer surface of said junction terminal to prevent displacement of said junction terminal from between said fingers, said spring force being induced by interaction between said collar and said fingers when said collar is moved to said advanced position and when said fingers are inhibited from flexing inwardly by said junction terminal, said spring force pressing tightly against said longitudinal wall, said spring force being continuous whenever said junction terminal is received between said fingers and said collar is in said advanced position, said connector being free from said spring force when said collar is in said advanced position and said junction terminal has not been received between said fingers, e. each said finger having a cam defined thereon, said collar engaging said cam upon displacement of said collar toward said advanced position, engagement by said collar deflecting at least the distal portion of the respective finger toward said flexed position.

15. A connector as in claim 14, wherein said fingers squeeze directly against said junction terminal wall.

* * * * *